(12) United States Patent
Hodgkinson

(10) Patent No.: US 9,968,352 B2
(45) Date of Patent: May 15, 2018

(54) CONCENTRIC BARBED SUTURE

(71) Applicant: Covidien LP, Mansfield, MA (US)

(72) Inventor: Gerald N. Hodgkinson, Guilford, CT (US)

(73) Assignee: Covidien LP, Mansfield, MA (US)

( * ) Notice: Subject to any disclaimer, the term of this patent is extended or adjusted under 35 U.S.C. 154(b) by 255 days.

(21) Appl. No.: 14/389,846

(22) PCT Filed: Nov. 18, 2013

(86) PCT No.: PCT/US2013/070476
§ 371 (c)(1),
(2) Date: Oct. 1, 2014

(87) PCT Pub. No.: WO2014/078757
PCT Pub. Date: May 22, 2014

(65) Prior Publication Data
US 2015/0073474 A1  Mar. 12, 2015

Related U.S. Application Data

(60) Provisional application No. 61/727,935, filed on Nov. 19, 2012.

(51) Int. Cl.
*A61B 17/04* (2006.01)
*A61B 17/06* (2006.01)
*A61B 17/00* (2006.01)

(52) U.S. Cl.
CPC .... *A61B 17/06166* (2013.01); *A61B 17/0469* (2013.01); *A61B 2017/00526* (2013.01); *A61B 2017/00889* (2013.01); *A61B 2017/00893* (2013.01); *A61B 2017/06171* (2013.01); *A61B 2017/06176* (2013.01); *Y10T 428/2931* (2015.01); *Y10T 428/2935* (2015.01); *Y10T 428/2938* (2015.01)

(58) Field of Classification Search
CPC .......... A61B 17/0469; A61B 17/06166; A61B 2017/00526; A61B 2017/06171; A61B 2017/06176; Y10T 428/2931; Y10T 428/2935; Y10T 428/2938
See application file for complete search history.

(56) References Cited

U.S. PATENT DOCUMENTS

| 8,118,834 B1 * | 2/2012 | Goraltchouk .... A61B 17/06166 606/228 |
| 2007/0005110 A1 | 1/2007 | Collier et al. |
| 2008/0312688 A1 | 12/2008 | Nawrocki et al. |
| 2010/0023055 A1 | 1/2010 | Rousseau |

(Continued)

FOREIGN PATENT DOCUMENTS

WO    WO2011/060446 A2    5/2011

OTHER PUBLICATIONS

International Search Report for PCT/US13/70476 date of completion is Feb. 26, 2014 (4 pages).

(Continued)

*Primary Examiner* — Robert Lynch

(57) ABSTRACT

A barbed suture and a method of forming a barbed suture are disclosed. The barbed suture includes a core fiber and a sheet, which can be monolithic or formed from a plurality of longitudinally extending fibers, which is placed around the core fiber.

20 Claims, 8 Drawing Sheets

(56) References Cited

U.S. PATENT DOCUMENTS

2011/0251640 A1* 10/2011 Lauria .............. A61B 17/06166
606/228
2012/0116449 A1 5/2012 Kirsch et al.
2013/0226234 A1* 8/2013 Avelar ............. A61B 17/06166
606/231

OTHER PUBLICATIONS

Supplementary European Search Report dated Aug. 8, 2016 in corresponding European Patent Application No. 13855101.5, 7 pages.

* cited by examiner

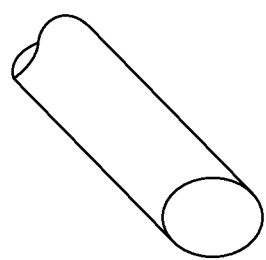
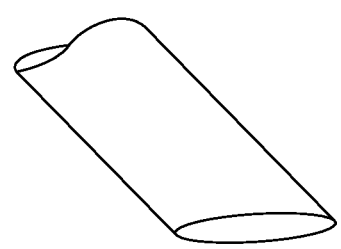
FIG. 2A            FIG. 2B
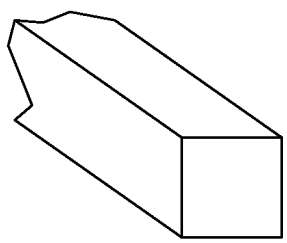
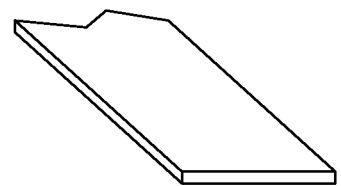
FIG. 2C            FIG. 2D
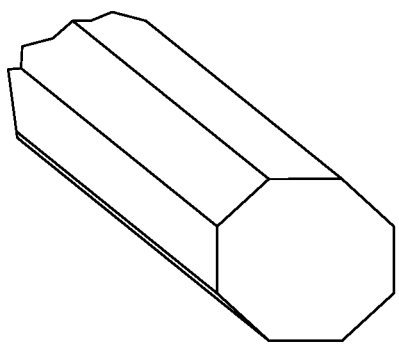
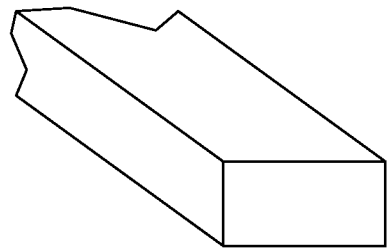
FIG. 2E            FIG. 2F

CONCENTRIC BARBED SUTURE

CROSS-REFERENCE TO RELATED APPLICATIONS

This application is a National Stage Application of PCT/US13/70476 under 35 U.S.C. § 371 (a), which claims priority of U.S. Provisional Patent Application Ser. No. 61/727,935 filed Nov. 19, 2012, the disclosures of each of the above-identified applications are hereby incorporated by reference in their entirety.

BACKGROUND

Technical Field

The present disclosure relates to barbed sutures and methods of forming barbed sutures.

Background of Related Art

Sutures are frequently used to close or bind wounds in human or animal tissue. Conventional sutures can be a smooth monofilament or can be a multi-filament, and can be formed from non-absorbable material such as silk, nylon, polyester, polypropylene, or cotton, or can be formed from bio-absorbable material such as glycolic and polymers and copolymers or lactic acid polymers and copolymers.

Barbed sutures are generally formed from the same materials as conventional sutures, and offer several advantages for closing wounds compared with conventional sutures. Barbed sutures include barbs that project from the surface of the suture body along the body length. The barbs are arranged to allow passage of the barbed suture in one direction through tissue but resist movement in the opposite direction.

Various methods of forming barbs on sutures are known in the art. However, current methods may be difficult or costly to achieve the desired arrangement and configuration of barbs on the suture. Accordingly, there is a continuing need for methods of forming barbs on a suture.

SUMMARY

Disclosed herein are barbed sutures and methods of forming barbed sutures. In embodiments, a barbed suture includes a core fiber, which defines an outer perimeter and a longitudinal axis. A sheet of biocompatible material including a plurality of barbs is positioned around the outer perimeter of the fiber. The barbs extend outwardly from the sheet in a first direction of less than 90 degrees with respect to the longitudinal axis. The core fiber may be a monofilament or multifilament fiber. In embodiments wherein the core is a multifilament fiber, the multiple filaments may be twisted, braided, commingled, intertwined, knitted and the like to form the multifilament core fiber. The width of the sheet may be equal to the circumference of the core fiber. The barbs may be positioned along any portion of the sheet and may be unidirectional, bidirectional and/or multidirectional. In embodiments, the barbs on the suture are symmetrical positioned about the longitudinal axis.

In embodiments, the sheet may further include a second plurality of barbs which extend outwardly from the sheet in a second direction that is less than 90 degrees with respect to the longitudinal axis. In embodiments, the second plurality of barbs may be positioned along a different portion of the sheet than the first plurality of barbs. In embodiments, the first plurality of barbs are positioned on a proximal end of the sheet and the second plurality of barbs are positioned on a distal end of the sheet.

In embodiments, the sheet may be formed from a monolithic material. In another embodiment, the sheet may be formed from a plurality of longitudinally extending fibers. The longitudinally extending fibers may be bonded to the core fiber at spaced intervals along the longitudinal axis. Each of the longitudinally extending fibers may define a first diameter, and the core fiber may define a second diameter, in which the first diameter is about 20% the value of the second diameter. The sheet, which is positioned around the circumference of the core fiber, may include a plurality of slots. The sheet may be bonded to the core fiber at a length away from each of the slots.

In embodiments, the barbed suture may include a multifilament core which defines an outer perimeter and a longitudinal axis. A sheet of biocompatible material including a plurality of barbs is positioned around the outer perimeter of the multifilament core. The barbs extend outwardly from the sheet in a first direction of less than 90 degrees with respect to the longitudinal axis.

Also disclosed is a method of forming a barbed suture. A core fiber defining an outer perimeter and a longitudinal axis is provided. Also provided is a sheet. A plurality of barbs is formed in the sheet, and the sheet is placed around the outer perimeter of the core fiber. The sheet may be formed from a monolithic material or may be formed from a plurality of fibers that may be longitudinally extending. In an embodiment, the sheet may define a tubular shape corresponding to that of the core fiber. The barbs may be formed by punching slots into the sheet.

In an embodiment, the sheet may include a plurality of slots, and the sheet may be bonded to the core fiber near each of the slots at a length away from each of the slots, i.e., at spaced intervals along the longitudinal axis of the core fiber. The core fiber and the sheet together define a first diameter. First portions of the sheet are compressed as the sheet is positioned around the core fiber, thereby reducing the first portions of the sheet to a second diameter that is smaller than the first diameter while second portions of the sheet such that the second portions protrude relative to the first portions, thereby defining the barbs. The slots in the sheet facilitate formation of the barbs by allowing the fibers of the sheet to bend relative to a longitudinal axis of the sheet.

These and other embodiments of the present disclosure will be described in greater detail hereinbelow.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiment(s) given below, serve to explain the principles of the disclosure, wherein:

FIGS. 2A-2F are perspective views of a suture having a circular (FIG. 2A), oval (FIG. 2B), rectangular (square) (FIG. 2C), flat (FIG. 2D), octagonal (FIG. 2E), and rectangular (FIG. 2F) cross-sectional profiles;

DETAILED DESCRIPTION

Figure 1A:
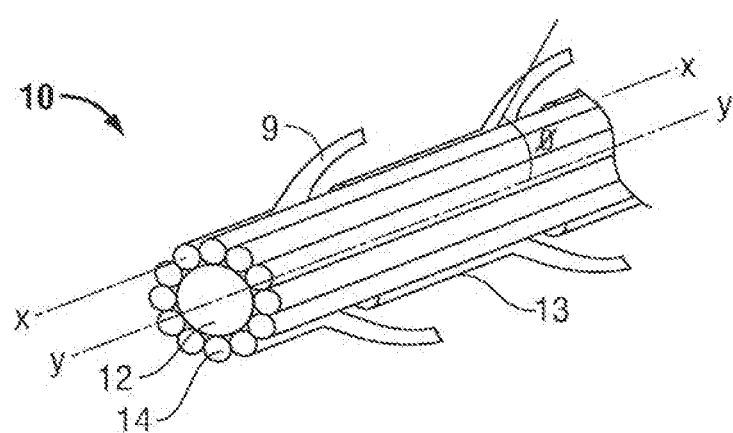
FIG. 1A is a perspective view of a suture in accordance with at least one embodiment of the present disclosure.

Particular embodiments of the present disclosure will be described herein with reference to the accompanying drawings. In the following description, well-known functions or constructions are not described in detail to avoid obscuring the present disclosure in unnecessary detail. As shown in the drawings and as described throughout the following description, and as is traditional when referring to relative positioning on an object, the term proximal refers to the end of the device that is closer to the user and the term distal refers to the end of the apparatus that is farther from the user.

Barbed sutures and methods of forming a barbed suture will be described herein with reference to FIGS. 1A-6B. As illustrated in FIG. 1A, suture 10 includes core fiber 12 and biocompatible sheet 13. Core fiber 12 defines an outer perimeter or circumference and a longitudinal axis y. Sheet 13 includes a plurality of longitudinally extending fibers 14 arranged concentrically around core fiber 12. Sheet 13 further includes a plurality of barbs 9 which extend outwardly to form barbed suture 10 and define a angle θ with respect to the longitudinal axis y of suture 10, thereby facilitating translation of suture 10 in one direction through tissue while inhibiting backward translation of suture 10 in the opposite direction. Although shown as a unidirectional barbed suture, the barbed sutures described herein may also be bidirectional and/or multidirectional barbed sutures.

In embodiments, the barbs extend outwardly to form barbed suture 10 and define an angle less than 90 degrees. In embodiments, the barbs extend outwardly to form barbed suture 10 and define an angle greater than 90 degrees. In embodiments, core fiber 12 is free of barbs.

Figure 1B:
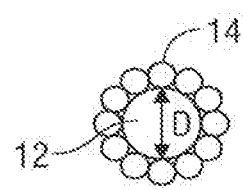
FIG. 1B is a cross-sectional view of the suture of FIG. 1A along line A-A.

As shown in FIG. 1B, longitudinally extending fibers 14 wrap exactly once around the circumference of core fiber 12. In such embodiments, an exact amount of longitudinally extending fibers 14 may be concentrically wrapped around the outer circumference of core fiber 12.

As further shown in FIG. 1B, core fiber 12 has a first diameter D and each of the longitudinally extending fibers 14 has a second diameter d. In embodiments, second diameter d of each of the longitudinally extending fibers 14 may represent from about 5% to about 50% of first diameter D of core fiber 12. In other embodiments, second diameter d of each of the longitudinally extending fibers 14 may represent from about 10% to about 40% of first diameter D of core fiber 12. In still other embodiments, second diameter d of each of the longitudinally extending fibers 14 may represent from about 15% to about 35% of first diameter D of core fiber 12. In particularly useful embodiments, second diameter d of longitudinally extending fibers 14 is about 20% of first diameter D of core fiber 12.

Although suture 10, core fiber 12 and/or the individual longitudinally extending fibers 14 are shown in FIGS. 1A and 1B as having a circular cross-sectional geometry, the cross-sectional geometry of suture 10, core fiber 12 and/or the individual longitudinally extending fibers 14 may be of any suitable shape. For example, FIGS. 2A-2F illustrate cross-sectional views of alternative non-limiting embodiments of the various cross-sectional geometries of suture 10, core fiber 12 and/or the individual longitudinally extending fibers 14, namely, round (FIG. 2A), elliptical (FIG. 2B), square (FIG. 2C), flat (FIG. 2D), octagonal (FIG. 2E), and rectangular (FIG. 2F).

In embodiments wherein the cross-sectional geometry may be a non-circular configuration, the use of the term circumference may be interpreted to include the outer perimeter of the non-circular configuration. In embodiments wherein the cross-sectional geometry may be a non-circular configuration, the use of the term diameter may be interpreted to include any straight line segment that passes through the center of the suture and whose endpoints are on the boundary of the outer perimeter of the suture.

Figure 3A:
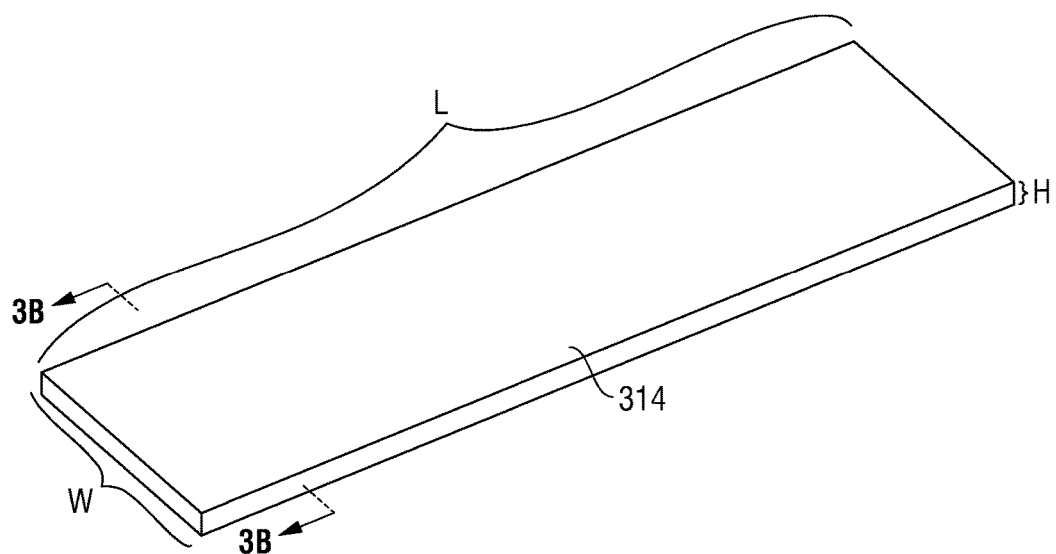
FIG. 3A is a perspective view of a biocompatible sheet in accordance with at least one embodiment of the present disclosure.
Figure 3B:
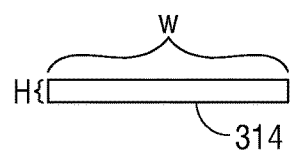
FIG. 3B is a cross-sectional view of the sheet of FIG. 3A along line A'-A'.

Turning now to FIGS. 3A-5B, the sutures described herein include biocompatible sheet 14. In embodiments, as shown in FIGS. 3A-3B, biocompatible sheet 314 may be preformed into a monolithic structure prior to being combined with the core fiber of the sutures described herein. Biocompatible sheet 314 includes a three-dimensional shape having a length L, width W and height H. In embodiments, the width W of sheet 314 is equal to the circumference of the core fiber so that sheet 314 may be concentrically wrapped about the outer circumference of the core fiber exactly once. In embodiments, the width W of sheet 314 may be less than the circumference of the core fiber so that multiple sheets 314 may be applied to the outer circumference of the core fiber.

Figure 4A:
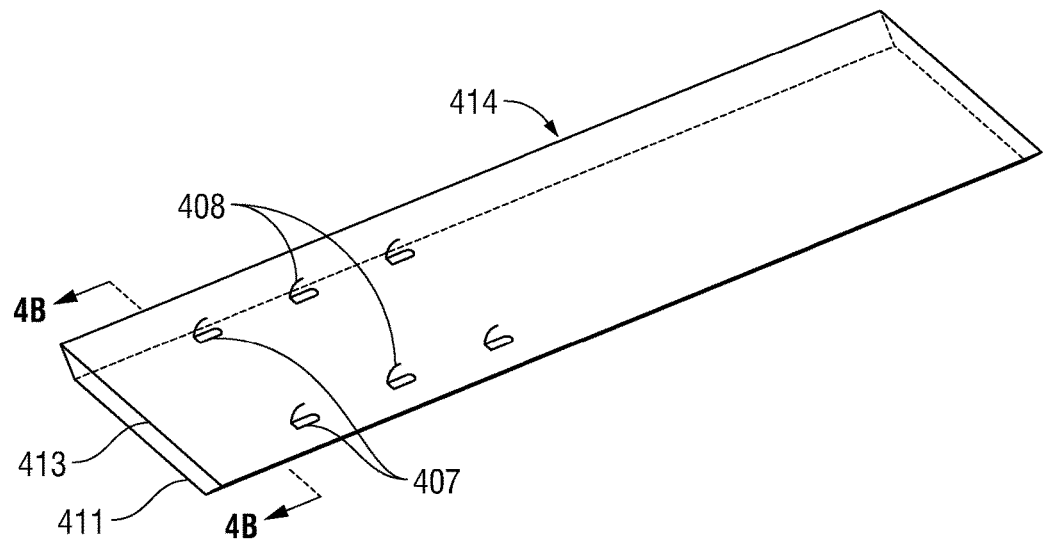
FIG. 4A is a perspective view of a biocompatible sheet in accordance with at least one embodiment of the present disclosure.
Figure 4B:
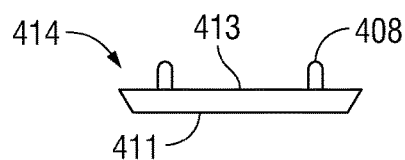
FIG. 4B is a cross-sectional view of the sheet of FIG. 4A along line B-B.
Figure 4C:
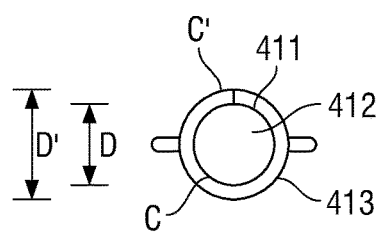
FIG. 4C is a front view of a suture described herein including the sheet of FIGS. 4A and 4B.

In FIGS. 4A-4C, biocompatible sheet 414 includes a base 411 which is shorter in width than top 413 thereby forming a trapezoidal shape cross-section (FIG. 4B). In embodiments, the shorter width of base 411 may be equal to the circumference C of core fiber 412 and the width of top 413 may be sufficient to compensate for the height of sheet 414 which when concentrically wrapped about core fiber 412 creates a circular design having a larger diameter D' and circumference C' than the diameter D and circumference C of core fiber 412.

As further illustrated in FIGS. 4A-4C, sheet 413 includes a plurality of slots 407 and barbs 408 symmetrically positioned along a portion of sheet 414. In embodiments, slots 407 and barbs 408 may be separated by about a distance equal to about half the width W of top 413 of sheet 414. In such embodiments, when sheet 414 is wrapped about the outer circumference of core fiber 412, slots 407 and barbs 408 will be positioned symmetrically on opposite side of the suture (FIG. 4C).

Figure 5A:
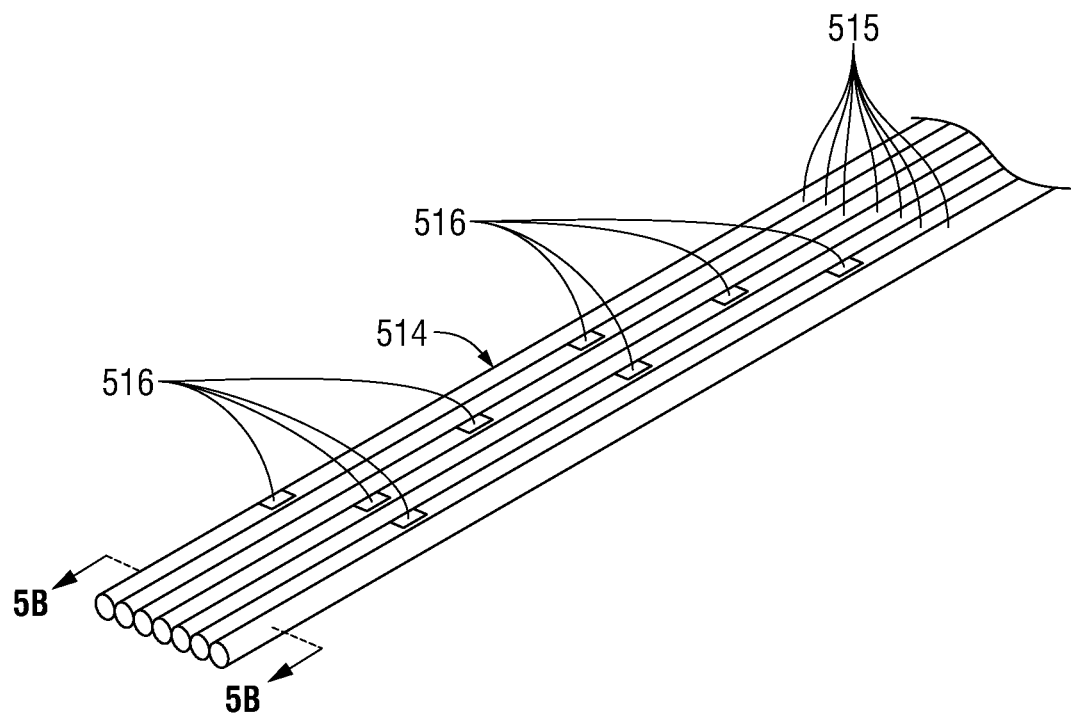
FIG. 5A is a perspective view of a biocompatible sheet in accordance with at least one embodiment of the present disclosure.
Figure 5B:
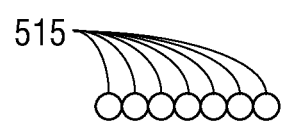
FIG. 5B is a cross-sectional view of the sheet of FIG. 5A along line X-X.

As depicted in FIGS. 5A-5B, biocompatible sheet 514 may a plurality of fibers 515 which may be combined to form biocompatible sheet 514 prior to being arranged about the core fiber. Biocompatible sheet 514 may further include slots 516 in any random, non-symmetrical configuration. It is envisioned that the portions of each fiber which are adjacent the slots may be further manipulated to form the barbs on the barbed sutures described herein. It is further envisioned that the barbs may be formed in the sheet at anytime prior, during and/or after the sheet and the core fiber are combined. For example, in certain embodiments, the barbs may be added and/or formed to the suture after the core fiber and the sheet are combined. In certain other embodiments, the barbs may be added to the sheet prior to being combined with the core fiber.

The barbed sutures described herein and any portion thereof, i.e., the core fiber, the biocompatible sheet, and/or the barbs, may be formed from any biocompatible material including any combination of natural, synthetic, biodegradable, and/or non-biodegradable material. The biocompatible materials may include biocompatible polymers, such as homopolymers or copolymers, including random copolymers, block copolymers, or graft copolymers. Biocompatible polymers may be a linear polymers, branched polymers or dendrimers.

The term "biodegradable" as used herein is defined to include both bioabsorbable and bioresorbable materials. By biodegradable, it is meant that the materials decompose, or lose structural integrity under body conditions (e.g. enzymatic degradation or hydrolysis) and/or are broken down (physically or chemically) under physiologic conditions in the body such that the degradation products are excretable and/or absorbable by the body.

Representative natural biodegradable polymers include: polysaccharides, such as alginate, dextran, chitin, hyaluronic acid, cellulose, collagen, gelatin, fucans, glycosaminoglycans, and chemical derivatives thereof (substitutions and/or additions of chemical groups, for example, alkyl, alkylene, hydroxylations, oxidations, and other modifications routinely made by those skilled in the art); and proteins, such as albumin, casein, zein, silk, and copolymers and blends thereof, alone or in combination with synthetic polymers.

Synthetically modified natural polymers include cellulose derivatives, such as alkyl celluloses, hydroxyalkyl celluloses, cellulose ethers, cellulose esters, nitrocelluloses, and chitosan. Examples of suitable cellulose derivatives include methyl cellulose, ethyl cellulose, hydroxypropyl cellulose, hydroxypropyl methyl cellulose, hydroxybutyl methyl cellulose, cellulose acetate, cellulose propionate, cellulose acetate butyrate, cellulose acetate phthalate, carboxymethyl cellulose, cellulose triacetate, and cellulose sulfate sodium salt. These are collectively referred to herein as "celluloses."

Representative synthetic degradable polymers include polyhydroxy acids prepared from lactone monomers, such as glycolide, lactide, caprolactone, ϵ-caprolactone, valerolactone, and δ-valerolactone, as well as pluronics, carbonates (e.g., trimethylene carbonate, tetramethylene carbonate, and the like), dioxanones (e.g., 1,4-dioxanone and p-dioxanone), 1,dioxepanones (e.g., 1,4-dioxepan-2-one and 1,5-dioxepan-2-one), and combinations thereof. Polymers formed therefrom include: polylactides; poly(lactic acid); polyglycolides; poly(glycolic acid); poly(trimethylene carbonate); poly(dioxanone); poly(hydroxybutyric acid); poly(hydroxyvaleric acid); poly(lactide-co-(ϵ-caprolactone-)); poly(glycolide-co-(ϵ-caprolactone)); polycarbonates; poly(pseudo amino acids); poly(amino acids); poly(hydroxyalkanoate)s; polyalkylene oxalates; polyoxaesters; polyanhydrides; polyorthoesters; and copolymers, block copolymers, homopolymers, blends, and combinations thereof.

Some non-limiting examples of suitable non-bioabsorbable materials from which the core fiber may be made include: polyolefins, such as polyethylene and polypropylene including atactic, isotactic, syndiotactic, and blends thereof polyethylene glycols; polyethylene oxides; ultra high molecular weight polyethylene; copolymers of polyethylene and polypropylene; polyisobutylene and ethylene-alpha olefin copolymers; fluorinated polyolefins, such as fluoroethylenes, fluoropropylenes, fluoroPEGSs, and polytetrafluoroethylene; polyamides, such as nylon and polycaprolactam; polyamines; polyimines; polyesters, such as polyethylene terephthalate and polybutylene terephthalate; aliphatic polyesters; polyethers; polyether-esters, such as polybutester; polytetramethylene ether glycol; 1,4-butanediol; polyurethanes; acrylic polymers and copolymers; modacrylics; vinyl halide polymers and copolymers, such as polyvinyl chloride; polyvinyl alcohols; polyvinyl ethers, such as polyvinyl methyl ether; polyvinylidene halides, such as polyvinylidene fluoride and polyvinylidene chloride; polyacrylonitrile; polyaryletherketones; polyvinyl ketones; polyvinyl aromatics, such as polystyrene; polyvinyl esters, such as polyvinyl acetate; copolymers of vinyl monomers with each other and olefins, such as etheylene-methyl methacrylate copolymers, acrylonitrile-styrene copolymers, ABS resins, and ethylene-vinyl acetate copolymers; alkyd resins; polycarbonates; polyoxymethylenes; polyphosphazine; polyimides; epoxy resins; aramids, rayon; rayon-triacetate; spandex; silicones; and combinations thereof.

The barbed sutures described herein and any portion thereof, i.e., the core fiber, the biocompatible sheet, and/or the barbs, may be formed using any technique within the purview of those skilled in the art, such as, for example, extrusion, molding, stamping, welding, rolling, annealing, calendaring, casting and/or spinning. In embodiments, the core fiber and the biocompatible sheet may be co-extruded. In some embodiments, the core fiber may include a multifilament yarn, which may contain multiple filaments of the same and/or different materials.

It is envisioned that any of the core fiber, sheet and/or barbs may be formed in a core/sheath, island-in-the-sea, and/or bicomponent configuration. Methods of forming such configurations into fibers or sheets are known to those skilled in the art.

In embodiments, wherein the sheet includes a plurality of elongated fibers, different materials may be used to form the individual fibers. For example, some of the fibers may include an ultra-high-molecular-weight material, such as, polyethylene, and some of the fibers may include a more flexible polymeric material, such as polylactides, polyglycolides, polycaprolactones, and the like. Such a combination of different elongated fibers may further enhance the strength of the outer sheet and the barbs, while also providing suitable handling characteristics, such as flexibility.

Figure 6A:
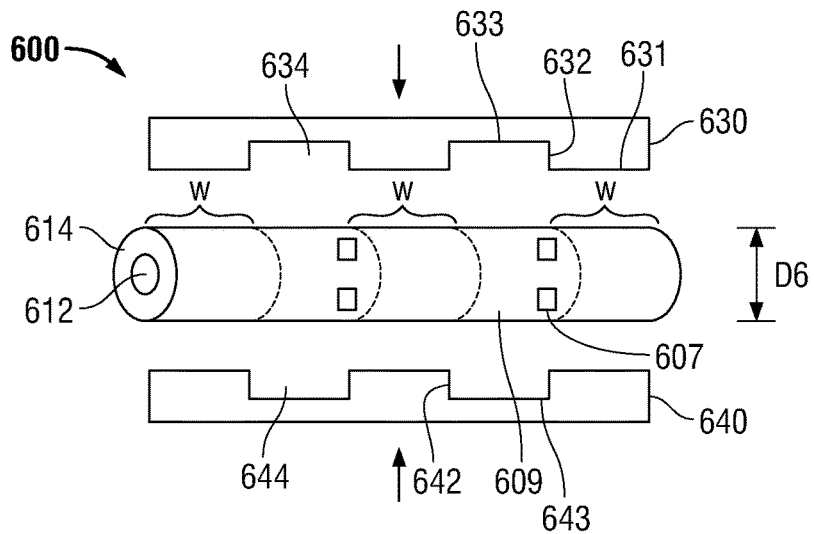
FIGS. 6A-6C are side views of a system described herein suitable for forming a barbed suture in accordance with at least one embodiment of the present disclosure.
Figure 6B:
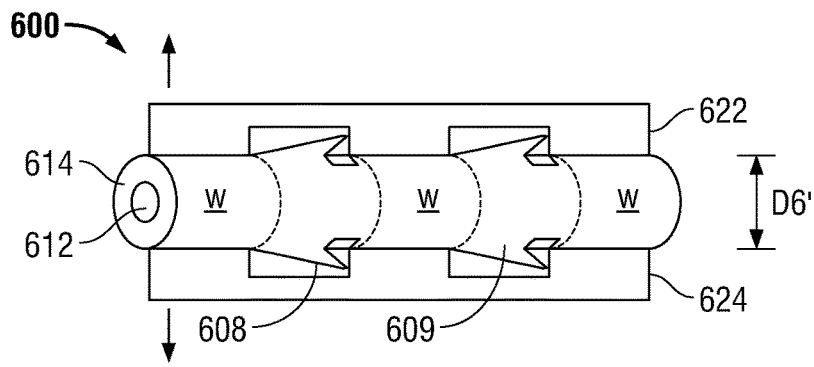
Figure 6C:
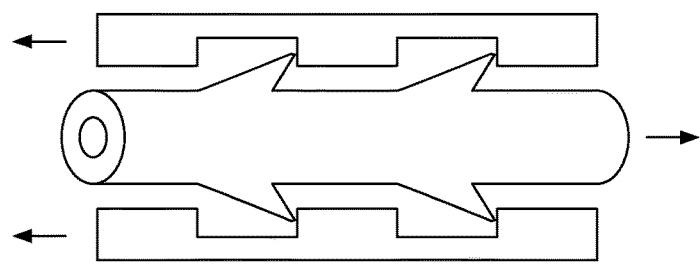

Turning now to FIGS. 6A-6C, a system 600 is illustrated for forming barbed suture 610 which includes a first press 630 and a second press 640 wherein the suture 610 is passed therethrough. Suture 610 includes core fiber 612 and sheet 614, which may include a plurality of elongated fibers, a plurality of slots 607 and a first diameter D6. First and second press 630 and 640, respectively, may be moved towards suture 610 as indicated by the arrows in FIG. 6A.

As illustrated FIG. 6B, outer surfaces 635 and 645 of first and second press 630 and 640, respectively, may be in contact with and/or slightly separated from the outer surface 610a of suture 610. First and second press 630 and 640 apply at least one of heat, pressure and/or energy to suture 610 thereby welding intermittent portions of sheet 614 to core fiber 612 and creating weld zone W and non-weld zone 609 along suture 610. In addition, the first diameter D6 of suture 610 is decreased along at least the weld zones W to produce a second smaller diameter D6'. As further depicted in FIG. 6B, decreased second diameter D6' in weld zone W forces a portion of sheet 614 in non-weld zone 607 and adjacent to slots 607 to protrude from and/or raise slightly above surface 610a of suture 610 to create barb 608. Barbs 608 are shown positioned within apertures 634, 644 of first and second press 630, 640, respectively. Apertures 634, 644 are each defined by a pair of sidewalls 632, 642 connected to each other via backwall 633, 643. First and second press 630, 640 may be moved away from surface 610a of suture 610 as indicated by the arrows in FIG. 6B.

With at least a portion of barbs 608 remaining positioned within apertures 634, 644, at least one of suture 610 and/or first and second press 630, 640 are moved longitudinally in a manner which forces barbs 608 against sidewalls 632, 642 to further raise barbs 608 away from surface 610a of suture 610 and creating a unidirectional barbed suture in which core fiber 612 is not cut or weakened by the formation of the barb. At which time first and second press 630, 640 may be further separated from suture 610 and suture 610 can be moved longitudinally away from the presses.

Figure 7A:
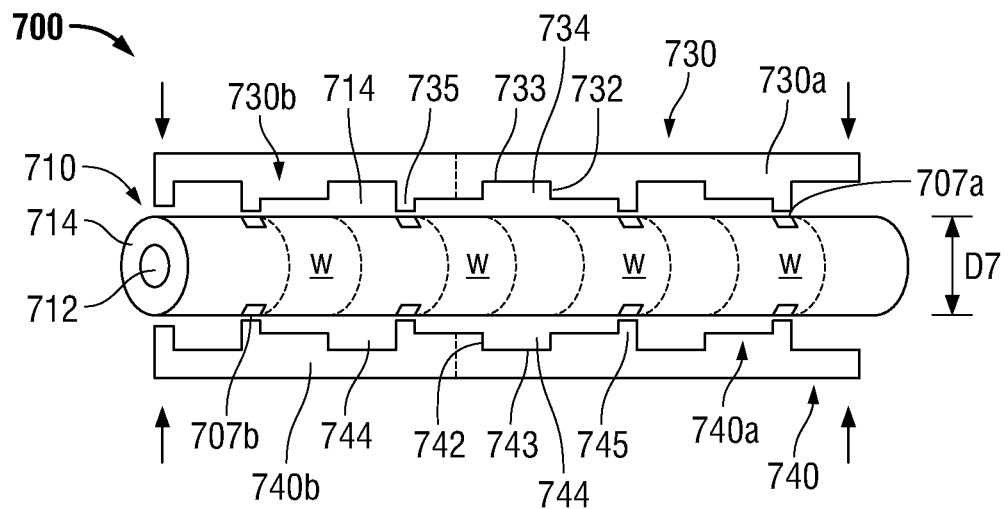
FIGS. 7A-7B are side views of a system described herein suitable for forming a barbed suture in accordance with at least one embodiment of the present disclosure; and, FIG. 8 is a schematic illustration of one process suitable for forming the barbed sutures described herein in at least one embodiment.
Figure 7B:
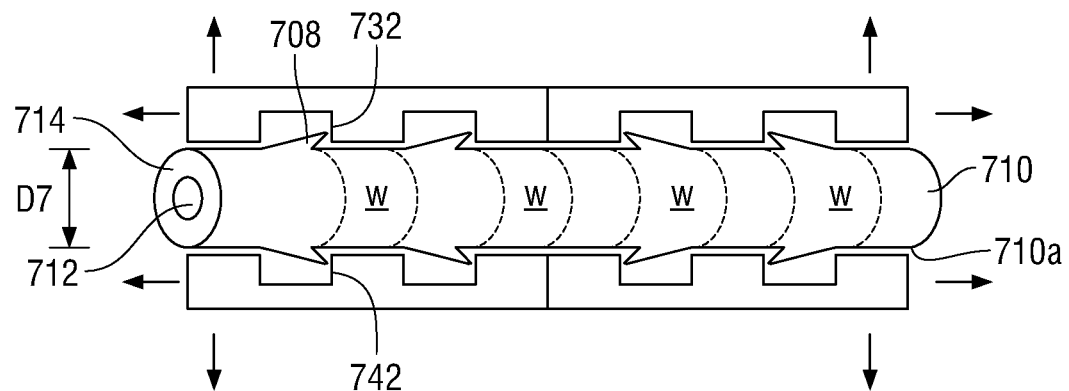

In FIGS. 7A and 7B, first and second press 730, 740 each include at least two separately movable portions 730a, 730b, 740a, 740b. Each movable portion 730a, 730b, 740a, 740b includes at least one aperture 734, 744 defined by a pair of sidewalls 732, 742 connected to each other via backwall 733, 743. Apertures 734, 744 further includes punch 735, 745 for creating punch slots 707a and 707b in sheet 714 of suture 710. It is envisioned that punch 735, 745 can be in a fixed position along first and second press 730, 740 and/or may be movable, such as a spring-loaded punch along first and second press 730, 740.

With at least a portion of barbs 708 positioned within apertures 734, 744, at least one of each of the separately movable portions 730a, 730b, 740a, 740b, of the first and second press 730, 740 are moved longitudinally as indicated by the arrows in FIG. 7B which forces barbs 708 against sidewalls 732, 742 to further raise barbs 708 away from surface 710a of suture 710 and creating a bidirectional barbed suture in which core fiber 712 is not cut or weakened by the formation of barb 708. First and second press 730, 740 may be further separated from suture 710 and suture 710 can be moved longitudinally away from the presses.

Figure 8:
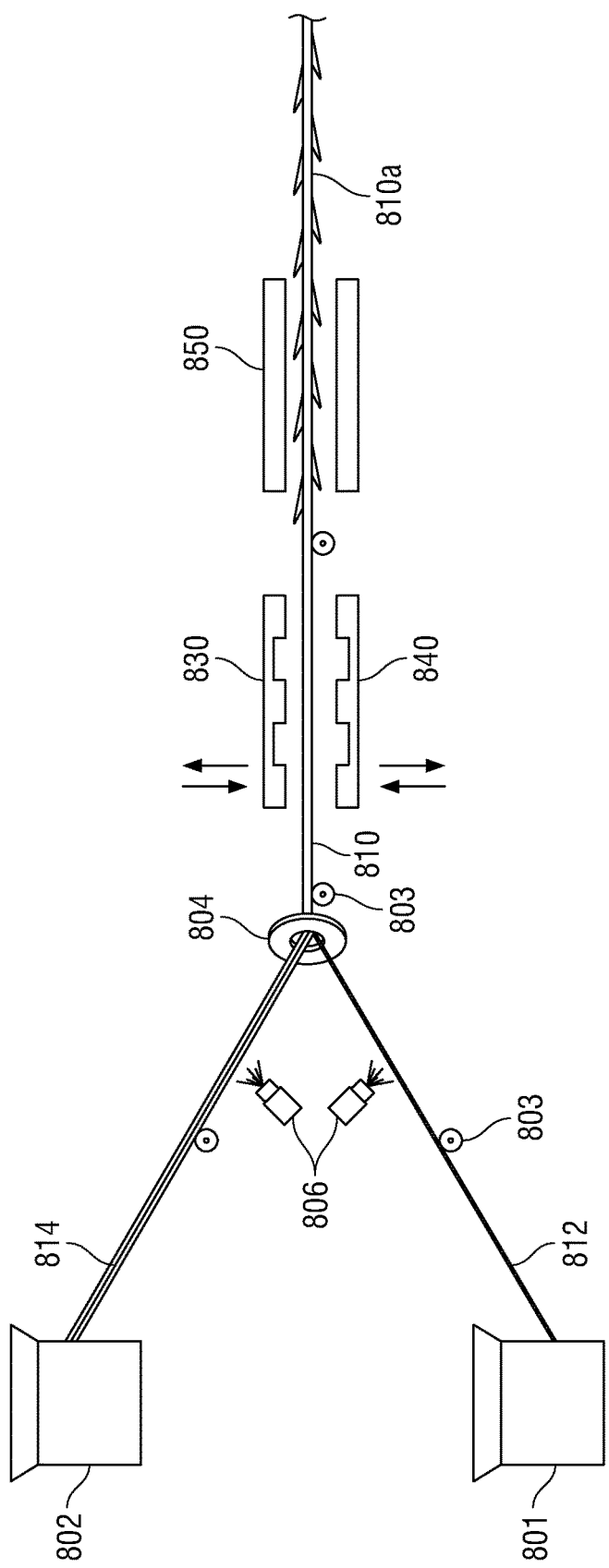

In some embodiments, as shown in FIG. 8, core fiber 812 and a plurality of elongated fibers 814 may be extruded, either separately or in combination to form suture 810. For example, core fiber 812 and a plurality of longitudinally elongated fibers 814 may exit a first and second extruder 801, 802, respectively and be passed over any number of suitable rollers 803 in any configuration suitable for making fibers.

Prior to passing through annulus 804, core fiber 812 and/or elongated fibers 814 may be coated with at least one bioactive agent, such as an adhesive to assist with securing elongated fibers 814 to core fiber 812. The coating may be applied using any suitable method known to those skilled in the art, such as dipping, spraying, and the like. As depicted in FIG. 8, at least one sprayer 806 is positioned between processors 801, 802 and annulus 804 to apply an optional coating containing a bioactive agent to the suture.

After passing over at least one roller 803, core fiber 812 and elongated fibers 814 may be passed through annulus 804 configured to wrap elongated fibers 814 around the outer circumference of core fiber 812. Although annulus 804 is shown including a circular opening, it is envisioned that any suitable geometric configuration may be used in annulus 804.

Suture 810 may then be passed through first and second presses 830 and 840 wherein suture 810, including core fiber 812 and longitudinally elongated fibers 814 are processed as described herein to further include slots and/or create barbs. After which, barbed suture 810a may be exposed to additional processing steps 850, such as drying, annealing, calendaring, sterilizing, packaging, and the like.

In embodiments, methods of forming a barbed suture include: providing a core fiber defining an outer perimeter and a longitudinal axis; providing a sheet of biocompatible material; placing the sheet around the outer perimeter of the core fiber; and, forming a plurality of barbs in the sheet after the core fiber and the sheet are combined.

In embodiments, the sheet may be wrapped around the outer perimeter of the core fiber. In embodiments, the sheet comprises a width equal to the outer perimeter of the core fiber. In embodiments, the sheet includes a base width and a top width wherein the base width is equal to the outer perimeter of the core fiber and the top width is greater than the outer perimeter of the core fiber.

In embodiments, the sheet may include slots prior to being placed about the core fiber. In embodiments, the slots may be added to the sheet after being placed about the core fiber. In embodiments, the barbs are only positioned on the sheet.

In embodiments, the core fiber and the sheet together define a first diameter, and the methods described herein further include compressing first portions of the sheet as the sheet is positioned around the core fiber, thereby reducing the first portions of the sheet to a second diameter that is smaller than the first diameter, while second portions of the sheet adjacent to the slots are not compressed such that the second portions protrude relative to the first portions, thereby defining the barbs.

As previously described, in some embodiments, the barbed sutures described herein may include an adhesive intermittently positioned along the length of the suture to strengthen the attachment between the sheet and the core fiber. Some non-limiting examples of suitable adhesives include methacrylates, acrylates, cyanoacrylates, fibrins, thrombins, celluloses, polysaccharides, and the like.

In addition, in some embodiments, the sutures described herein, including any portion thereof, such as the core fiber, the biocompatible sheet, the barbs, and any additional coating or adhesive may include at least one bioactive agent. Suitable bioactive agents include, for example, biocidal agents, antimicrobial agents, antibiotics, anti-proliferatives, medicants, growth factors, anti-clotting agents, clotting agents, analgesics, anesthetics, anti-inflammatory agents, wound repair agents and the like, chemotherapeutics, biologics, protein therapeutics, monoclonal or polyclonal antibodies, DNA, RNA, peptides, polysaccharides, lectins, lipids, probiotics, diagnostic agents, angiogenics, anti-angiogenic drugs, polymeric drugs, and combinations thereof.

Bioactive agents include substances which are beneficial and tend to promote the healing process. For example, the barbed sutures can be provided with a bioactive agent that will be deposited at the sutured site. The bioactive agent can be chosen for its antimicrobial properties, capability for promoting wound repair and/or tissue growth, or for specific indications such as thrombosis.

The term "antimicrobial agent" as used herein includes an agent which by itself or through assisting the immune system, helps the body destroy or resist microorganisms which may be pathogenic. An antimicrobial agent includes antibiotics, antiseptics, quorum sensing blockers, antifungals, anti-virals, surfactants, metal ions, antimicrobial proteins and peptides, antimicrobial polysaccharides, disinfectants and combinations thereof. Antimicrobial agents which are slowly released into the tissue can be applied in this manner to aid in combating clinical and sub-clinical infections in a surgical or trauma wound site. In embodiments, suitable antimicrobial agents may be soluble in one or more solvents.

Although the above bioactive agents have been provided for the purposes of illustration, it should be understood that the present disclosure is not so limited. In particular, although certain bioactive agents are specifically referred to above, the present disclosure should be understood to include analogues, derivatives and conjugates of such agents.

Bioactive agents may be applied onto the suture and/or the adhesive coating utilizing any method within the purview of one skilled in the art including, for example, spraying, dipping, brushing, rolling, wiping, painting, extruding, ultrasonics, and the like. In embodiments, a bioactive agent may be deposited within the barb angles, that is, the angle formed between the barbs and the elongate body of the sutures. In embodiments, the bioactive agent may be positioned within the slot(s).

In embodiments, the sutures may also be dyed in order to increase the visibility of the suture in the surgical field. Any dye suitable for incorporation in medical devices may be used. Such dyes include, but are not limited to, carbon black, bone black, D&C Green No. 6, and D&C Violet No. 2. Fibers in accordance with the present disclosure may be dyed by adding dye in an amount up to about a few percent; in other embodiments, they may be dyed by adding dye in an amount of about 0.2%; in still further embodiments, the dye may be added in an amount from about 0.06% to about 0.08%.

In use, the barbed sutures described herein may include a needle (not shown) on the proximal and/or distal end thereof. The new barbed sutures described herein should approximate tissue quickly with appropriate tension, alleviate distortion of tissue, and help to minimize scarring, due to the self-retaining benefits imparted by the barbs and be stronger than other barbed sutures since the core fiber has not be damaged in order to form the barb.

The new barbed sutures would be especially useful in surgeries where minimization of scarring is imperative, such as cosmetic surgery, as well as in surgeries where space is limited, such as endoscopic surgery or microsurgery. Some non-limiting examples include cosmetic surgery, hernia repair, gastric banding procedures, vaginal prolapse and the like.

In addition, the barbed sutures may be combined with any other suitable surgical implant, such as a mesh, sling, pledget, buttress, and the like.

Although the illustrative embodiments of the present disclosure have been described herein with reference to the accompanying drawings, it is to be understood that the disclosure is not limited to those precise embodiments, and that various other changes and modifications may be effected therein by one skilled in the art without departing from the scope or spirit of the disclosure. For example, it should be understood that sutures having barbs having different configurations, e.g., shapes, number, and orientation, are in the spirit of the present disclosure.

What is claimed is:

1. A barbed suture comprising:
   a core fiber defining an outer perimeter, a length, and a longitudinal axis; and
   a sheet positioned around the outer perimeter of the core fiber, the sheet including a plurality of longitudinally extending fibers aligned concentrically around the core fiber along the length of the core fiber and a plurality of slots, each slot separating a first portion of an individual fiber of the plurality of longitudinally extending fibers from a second portion of the individual fiber, wherein the first portion of the individual fiber is separate from the second portion of the individual fiber and the first portion is bent relative to the longitudinal axis to form a barb extending outwardly from the sheet in a first direction of less than 90 degrees with respect to the longitudinal axis.

2. The barbed suture of claim 1, wherein the core fiber is a monofilament fiber.

3. The barbed suture of claim 1, wherein the core fiber is a multifilament fiber.

4. The barbed suture of claim 1, wherein the sheet further comprises a second plurality of barbs extending outwardly from the sheet in a second direction that is less than 90 degrees with respect to the longitudinal axis.

5. The barbed suture of claim 1, wherein the sheet comprises a width equal to the outer perimeter of the core fiber.

6. The barbed suture of claim 1, wherein the barbed suture is a multidirectional barbed suture.

7. The barbed suture of claim 1, wherein the plurality of longitudinally extending fibers are bonded to the core fiber at spaced intervals along the longitudinal axis.

8. The barbed suture of claim 1, wherein each of the individual longitudinally extending fibers defines a first diameter and the core fiber defines a second diameter, the first diameter having a value about 20% that of the second diameter.

9. The barbed suture of claim 1, wherein the sheet is bonded to the core fiber at a length away from the plurality of slots.

10. The barbed suture of claim 1, wherein the core fiber is not cut by the formation of the barb.

11. The barbed suture of claim 1, wherein the suture further comprises a first zone having a first diameter and including at least one slot of the plurality of slots and a second zone including the second portion of the individual fiber, the second zone having a second diameter smaller than the first zone.

12. The barbed suture of claim 11 wherein the second zone is bonded to the core fiber.

13. The barbed suture of claim 12 wherein the first zone is not bonded to the core fiber.

14. The barbed suture of claim 13 wherein the second zone is a weld zone wherein the second zone is welded to the core fiber.

15. A barbed suture comprising:
   a multifilament core defining a length and a longitudinal axis,
   a sheet wrapped around the multifilament core, the sheet including a plurality of longitudinally extending fibers aligned concentrically around the core fiber along the length of the core fiber and a plurality of slots, each slot separating a first portion of an individual fiber of the plurality of longitudinally extending fibers from a second portion of the individual fiber, wherein the first portion of the individual fiber is separate from the second portion of the individual fiber and the first portion is bent relative to the longitudinal axis to form a barb extending outwardly from the sheet in a first direction of less than 90 degrees with respect to the longitudinal axis.

16. The barbed suture of claim 15, wherein the multifilament core is selected from the group consisting of twisted, braided, comingled, and intertwined filaments.

17. The barbed suture of claim 15, wherein the sheet further comprises a second plurality of barbs extending outwardly from the sheet in a second direction that is less than 90 degrees with respect to the longitudinal axis.

18. The barbed suture of claim 15, wherein the plurality of longitudinally extending fibers are bonded to the core fiber at spaced intervals along the longitudinal axis.

19. The barbed suture of claim 15, wherein each of the individual longitudinally extending fibers defines a first diameter and the core fiber defines a second diameter, the first diameter having a value about 20% that of the second diameter.

20. The barbed suture of claim 15, wherein the sheet is bonded to the core fiber at a length away from the plurality of slots.

\* \* \* \* \*